(12) United States Patent
Grigorov et al.

(10) Patent No.: US 8,637,296 B2
(45) Date of Patent: Jan. 28, 2014

(54) LACTOBACILLUS HELVETICUS STRAINS FOR PRODUCING HYPOTENSIVE PEPTIDES

(75) Inventors: Martin Grigorov, Epalinges (CH); Jacques-Edouard Germond, Crissier (CH); Sylvie Tournade, Caen (FR); Michael Affolter, Savigny (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 12/997,777

(22) PCT Filed: Jun. 8, 2009

(86) PCT No.: PCT/EP2009/004092
§ 371 (c)(1),
(2), (4) Date: Dec. 13, 2010

(87) PCT Pub. No.: WO2009/149880
PCT Pub. Date: Dec. 17, 2009

(65) Prior Publication Data
US 2011/0165135 A1   Jul. 7, 2011

(30) Foreign Application Priority Data
Jun. 12, 2008 (EP) .................................. 08158092

(51) Int. Cl.
*C12N 1/20* (2006.01)
(52) U.S. Cl.
USPC ........................ 435/252.9; 424/93.45
(58) Field of Classification Search
None
See application file for complete search history.

(56) References Cited

U.S. PATENT DOCUMENTS 6,890,529 B1 * 5/2005 Mayra-Makinen et al. ...................... 424/93.45

FOREIGN PATENT DOCUMENTS

| EP | 1 908 354 | 4/2008 | | |
|---|---|---|---|---|
| WO | 0132905 | 5/2001 | | |
| WO | 2004098309 | 11/2004 | | |
| WO | WO2004/098309 | * 11/2004 | ............... | A23J 3/34 |
| WO | WO 2004098309 A1 | * 11/2004 | ............... | A23J 3/34 |
| WO | 2006084573 | 8/2006 | | |

OTHER PUBLICATIONS

Seppo et al., A fermented milk high in bioactive peptides has a blood pressure-lowering effect in hypertensive subjects, 2003, Am. J. Clin. Nutr. 77(2): 326-330.*
Huth et al., Major Scientific Advances with Dairy Foods in Nutrition and Health, 2006, J. Dairy Sci. 89: 1207-1221.*
Jauhiainen et al., "Lactobacillus helveticus fermented milk reduced arterial stiffness in hypertensive subjects," International Dairy Journal, vol. 17 (2007), pp. 1209-1211-XP 22170499.
Hong et al., "The antihypertensive effect of peptides: A novel alternative to drugs?," Peptides, vol. 29 (2008) pp. 1062-1071-XP 022646994.
Jauhiainen et al., "Lactobacillus helveticus Fermented Milk Lowers Blood Pressure in Hypertensive Subjects in 24-h Ambulatory Blood Pressure Measurement," American Journal of Hypertension, Ltd. (2005), vol. 18 (2005), pp. 1600-1605-XP 05215084.

* cited by examiner

*Primary Examiner* — Jon P Weber
*Assistant Examiner* — Robert Yamasaki
(74) *Attorney, Agent, or Firm* — K&L Gates LLP

(57) ABSTRACT

The present invention relates to novel strains of *Lactobacillus helveticus* that can produce high amounts of hypotensive peptides, in particular IPP, VPP and LPP. It also relates to a fermented milk product containing a mixture of tripeptides IPP-VPP-LPP and a strain of *L. helveticus*. The invention further relates to the specific peptide mixture consisting of tripeptides IPP, VPP and LPP and the use of the fermented product or mixture of peptides in food products, food supplement or pharmaceutical compositions for reducing or preventing hypertension.

13 Claims, 2 Drawing Sheets

LACTOBACILLUS HELVETICUS STRAINS FOR PRODUCING HYPOTENSIVE PEPTIDES

The present invention relates to novel strains of *Lactobacillus helveticus* that can produce high amounts of hypotensive peptides, in particular IPP, VPP and LPP. It also relates to a fermented milk product containing a mixture of tripeptides IPP-VPP-LPP and a strain of *L. helveticus*. The invention further relates to the specific peptide mixture consisting of tripeptides IPP, VPP and LPP and the use of the fermented product or mixture of peptides in food products, food supplement or pharmaceutical compositions for reducing or preventing hypertension.

BACKGROUND OF THE INVENTION

Hypertension or high blood pressure is considered to be one of the main risk factors for Cardio Vascular Diseases. One of the mechanisms which regulates blood pressure is the renin-angiotensin system. This is a cascade of reactions leading to the formation of angiotensin II, which has a strong vasoconstrictive and hence blood pressure increasing effect. Inhibition of one of the key enzymes in this cascade: Angiotensin I Converting Enzyme (ACE) reduces formation of angiotensin II and thus has a blood pressure lowering effect.

The degradation of milk proteins with proteinases from *Lactobacillus helveticus* which has been employed for producing fermented milk for a long time as a typical lactic acid bacteria starter for dairy milk products, produced peptides with ACE-inhibiting activity that had a significant antihypertensive effect in spontaneously hypertensive rats (Yamamoto, Akino, & Takano, 1994). The same effect was observed with fermented milk containing *L. helveticus* (Nakamura, Yamamoto, Sakai, Okubo et al., 1995).

In fact, it has now been showed that milk fermented with *Lactobacillus helveticus* (*L. helveticus*) contains small peptides such as isoleucyl-prolyl-proline (Ile-Pro-Pro, IPP) and valyl-prolyl-proline (Val-Pro-Pro, VPP), which inhibit the angiotensin converting enzyme (ACE).

A commercially available fermented milk product, which claims to be "suitable for those with mild hypertension" is Calpis sour milk, fermented with *Lactobacillus helveticus* and *Saccharomyces cervisiae*, produced by Calpis Food Industry, Japan.

Another commercially available fermented milk product is EVOLUS™ produced by Valio, Finland, which claims to be the first European functional food to "help lower blood pressure".

Both fermented milk products are fermented with *Lactobacillus helveticus* strains. The products contain bioactive peptides (VPP and IPP) responsible for in vitro ACE inhibition, which are produced by proteolysis of caseins. Compared to other lactic acid bacteria *L. helveticus* is one of the most efficient proteolytic *Lactobacillus* species.

However, there is still a need for alternative lactic bacteria strains of the genus *L. helveticus* that has a particular high production of hypotensive peptides that can be prepared easily and provided to consumers in an agreeable form to take.

SUMMARY OF THE INVENTION

It is thus an object of the present invention to provide a fermented milk product a of *Lactobacillus helveticus* and a mixture of IPP-VPP-LPP or mixture of IPP, VPP and LPP obtainable with said strains. Said mixture of IPP-VPP-LPP is preferably in ratio from about 2:1:1 to 1:1:1. Such peptides having anti-hypertensive properties can be added to food or pharmaceutical products to prevent or reduce hypertension.

It is another object of the present invention to provide novel lactic acid bacteria strains of *Lactobacillus helveticus*, namely NCC 935 (CNCM I-3997), NCC 1322 (LH111) (CNCM I-3998) and NCC 1649 (LH158) (CNCM I-3999) which can produce a mixture of tripeptides consisting of VPP, IPP and LPP. Moreover, they can provide two fold higher than the concentration found in the commercial product Ameal S™.

According to the present invention, there is also provided a food, pet food composition or nutritional supplement containing a fermented milk comprising the aforementioned lactic acid bacteria, and/or a tripeptide mixture consisting of Val-Pro-Pro, Ile-Pro-Pro and Leu-Pro-Pro, said mixture being preferably in a ratio from about 2:1:1 to 1:1:1. In a last object, the invention relates to the use of such food, petfood or food supplement for their anti-hypertensive properties.

In the figures.

DETAILED DESCRIPTION OF THE INVENTION

Figure 1:
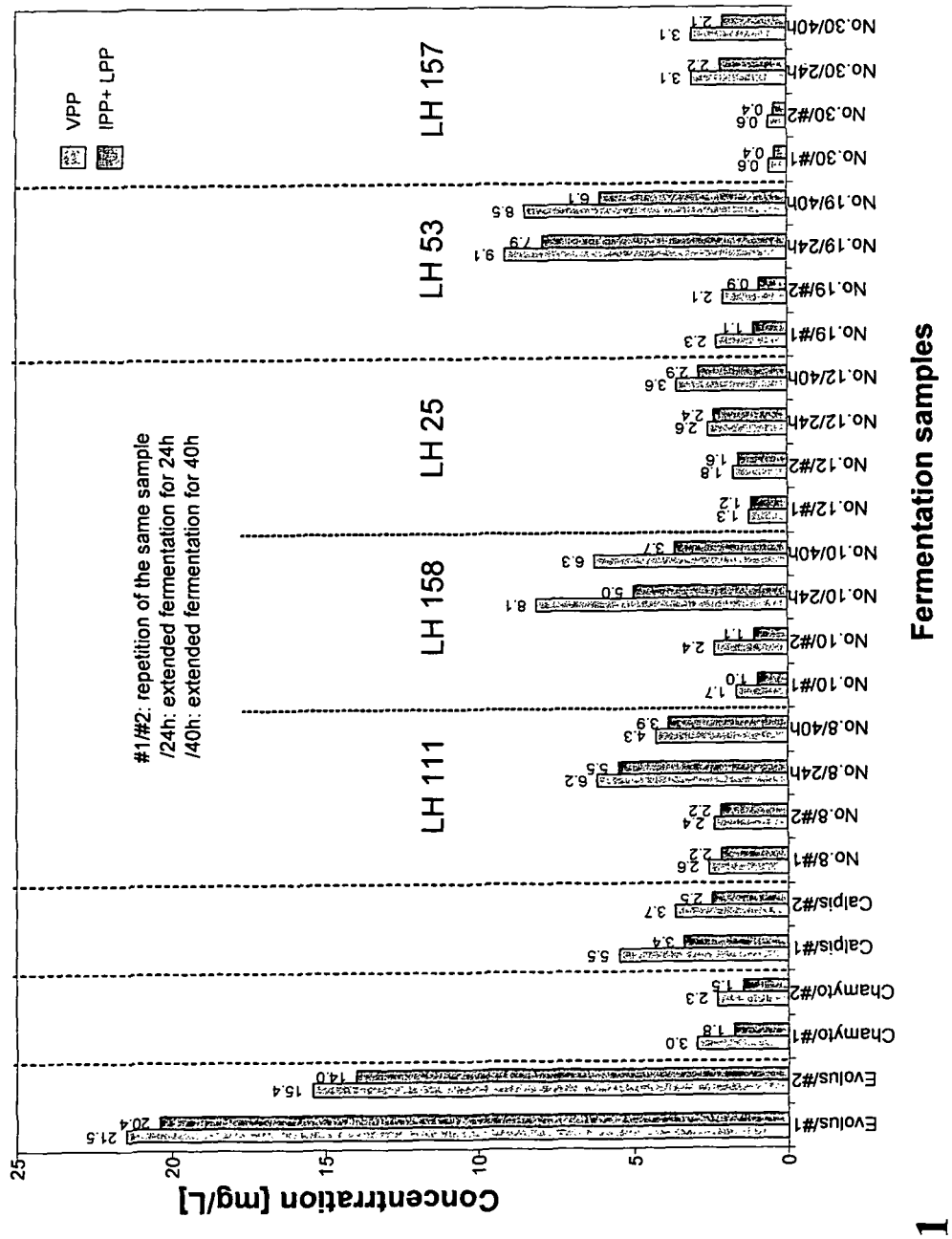
FIG. 1 shows concentration of VPP and IPP tripeptides present in different commercial dairy products and generated in milk by fermentation using different strains of *Lactobacillus helveticus*.
Figure 2:
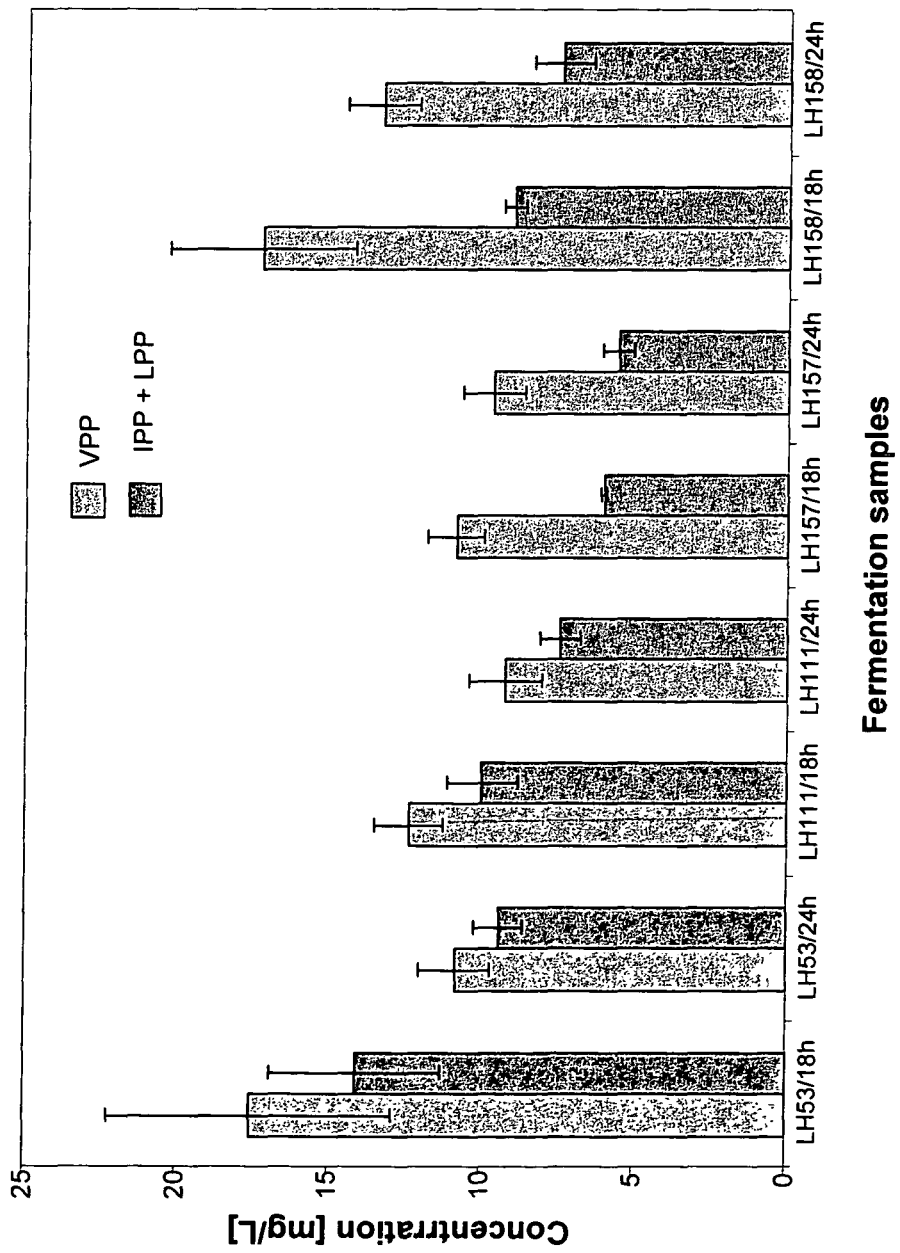
FIG. 2 shows concentration of VPP and IPP tripeptides present in a conventional diluted milk base, after fermentation with *L. helveticus* LH53, LH111, LH158, LH157 18 h and 24 h.

Within the context of this specification the word "comprises" is taken to mean "includes, among other things". It is not intended to be construed as "consists of only". Also, "tripeptides VPP, IPP and LPP" as defined herein include VPP, IPP and LPP and peptides containing 3-25 amino acid residues including the sequence VPP, IPP and VPP, and mixtures of these peptides.

According to a first object, a fermented milk product comprising a lactic acid bacteria strain of *Lactobacillus helveticus* and a mixture of IPP-VPP-LPP is concerned.

In fact, it has been surprisingly found that some strains of *L. helveticus* can produce a large amount of a mixture of three tripeptides VPP-IPP-LPP, preferably in a ratio varying upon fermentation conditions, from about 2:1:1 to 1:1:1.

Among all the strains tested, *L. helveticus* NCC 935 (LH53), NCC1322 (LH111) and NCC1649 (LH158) have been deposited by way of examples, according to the Budapest Treaty at the Collection Nationale de Culture de Microorganisms (CNCM) at Pasteur Institute (France), 28 rue du Docteur Roux, 75724 Paris Cedex 15, on Jun. 11, 2008 under the references CNCM I-3997, CNCM I-3998 and CNCM I-3999, respectively.

The fermented milk product according to the invention can be prepared by a process comprising fermenting a medium containing a protein-based starting material containing the sequence VPP, IPP and LPP, with the lactic acid bacteria described above. Preferably milk is used as starting material.

The milk starting material may be any milk, skimmed milk as long as it contains a protein comprising the amino acid sequence VPP, IPP and/or LPP. Animal milk such as cow's milk, goat's milk, camel milk, horse's milk, may also be used.

The content of the solid in the milk starting material is not particularly limited, but is usually 5 to 20 wt %. The milk starting material may be reconstituted milk, prepared by mixing water and milk ingredients, for instance (skim) milk powder. The milk starting material may contain additives, such as carbohydrates, etc. as long as these additives do not interfere with the fermentation.

Fermentation of the milk starting material may be executed in conventional fermentors, in which the milk starting material as a medium is inoculated with the *L. helveticus* of the present invention. The *L. helveticus* may be added to the fermentation preferably in the form of a pre-cultured starter having sufficient activity. The initial cell count of the starter is preferably about $10^7$ to $10^9$ cells/ml. There is no particular limitation on the amount of the *L. helveticus* with which the medium is inoculated but it is preferably from 1 to 5%, most preferably 2% of starter strain.

The materials in the fermentor, including *L. helveticus* inoculum and the milk starting material, may be mixed in conventional way, in order to achieve a homogeneous fermentation medium.

The fermentation advantageously may be performed at 25 to 50° C., preferably 30 to 45° C., for 6 to 100 hours, preferably 15 to 50 hours. In a most preferred embodiment, the fermentation temperature is of 38-42° C., since in this temperature range the highest amount of tripeptides VPP, IPP and LPP is formed. Also, the pH during fermentation may be adjusted so that the highest amount of tripeptides is generated.

The total amount of tripeptides produced according to the present invention in the fermented milk may vary upon the source of milk used as starting material and optimized process conditions. Such amount may be comprised from about 10 to 50 mg/l of total tripeptides, preferably from 15 to 30 mg/l, for example. Also, dilutions which are usually carried out for the preparation of diluted fermented milk drinks will obviously lower the total amount of tripeptides. In case of preparation of conventional diluted milk drinks, the amount of total tripeptides may be at maximum of about 10 mg/L of fermented milk drink, preferably from 4 to 8 mg/L.

The stability of the tripeptides during storage at 8° C. for one month was measured and the results show that the concentration of the tripeptides after storage is only slightly lower than at the end of fermentation, thus indicating that the peptides are not degraded during storage at 8° C.

In another embodiment, the fermented milk, optionally pasteurised, could be supplemented with a micro-organism according to the present invention, which will not further grow on the fermented medium. For example, the product may be a yoghurt, which is heat-treated and to which micro-organisms which are not able to grow on the fermented, heat-treated product are added, in order to obtain a product which fulfils the features of the present invention. Accordingly, the product according to the present invention may be stirred or set yoghurt, which is natural or which has additional flavours or ingredients, for example fruits. The product according to the invention could also be a shelf stable fresh cheese.

Other micro-organisms may optionally be added to the fermentation medium, such as probiotic bacteria or yeasts.

The fermented milk product may be used as such, or may be diluted, it may be concentrated, it may be purified and it may be dried, preferably spray-dried or freeze-dried. The fermented milk product may be a yogurt, an acidic milk beverage or cheese, for example. The fermented milk may also be used in a food product as a food ingredient. The food products according to the invention may be of any food type, pet food or nutritional supplement. Products according to the invention can be prepared by the skilled person based on common general knowledge, using fermented milk or fermented milk derived products such as the mixture IPP-VPP-LPP as described above, as an ingredient in suitable amounts. Examples of such food products are baked goods, nutritional compositions, and dairy type foods, in particular low-fat dairy products, snacks, drink, foods containing fermented sour milk, cereal based products, etc.

The fermented milk product according to the invention or food products derived may be pasteurized or sterilised.

Alternatively, the products according to the present invention may be syrup, a drink, a juice, such as an apple, orange or generally fruit juice, for example. The products may also be a soy-based product or cereal-based product. For example, it may be a soy-milk or a soy-drink. For example, the liquid product may be a soy-based replacement for milk. The soy-based product may be free of lactose.

They may comprise common food ingredients in addition to the fermented milk product, such as flavour, sugar, fruits, minerals, vitamins, stabilisers, thickeners, etc. in appropriate amounts.

In a preferred embodiment, additional active ingredient can be added to the compositions. Such ingredients are preferably Vitamin D or Vitamin D analogs.

The addition of Vitamin D in combination with the mixture of tripeptides according to the present invention improves the efficacy of the composition. The daily value DV for Vitamin D is of about 400 IU (for adults).

According to a further aspect, the present invention provides a method for preventing or treating hypertension using an effective amount of the fermented medium of *L. helveticus* strains as described above and/or their mixture of IPP-VPP-LPP, preferably in ratio 1:1:1 (+/−10%). Effective amount of the food according to the present invention may usually be, for example, so that the daily intake of total tripeptides is of at least 5.2 mg per day. As an example, with more than 30 mg/L tripeptides produced by fermentation of LH53, a fermented diluted milk base can contain the daily dose in 150 ml, for example.

Specific examples of the invention are now given as further illustration.

Example 1

Screening of LAB Strains

The aim of this work was to screen a series of lactic acid bacteria (LAB) strains for their potential to generate higher amount of bioactive tripeptides during milk fermentation.

A series of 30 strains of *Lactobacillus helveticus*, *Lactobacillus delbrueckii* subsp. *bulgaricus* and *Streptococcus thermophilus* were selected on the basis of their physiological characteristics. The first criteria considered was the acidification power (PA) which is the amount of acid produced in 24 h. This potential to produce large amount of acid is directly linked to growth behaviour and to the proteolytic properties of the bacteria in milk. An efficient proteolytic system is essential for the release of peptides. The second criteria considered was the peptidase activity of the strains, which may play a role on the production and/or stability of the peptides.

The different strains were reactivated from lyophilized stock in PA milk (10% skimmed milk powder, pasteurized at 98-100° C.° for 35 min). PA milk was then inoculated with 2% of each starter strains and incubated at 40° C. For each strain, fermentation was stopped at coagulation and stored at 4° C. The fermented products were then processed for the quantification of VPP and IPP as described below.

Quantification of the Tripeptides VPP and IPP by Liquid Chromatography (LC) and Mass Spectrometry (MS)
Sample Preparation The different fermented products were clarified (removal of the coagulated proteins) by centrifugation and the clear supernatant was stored in aliquots at −20° C. Aliquots of 500 μl of the clear supernatant were filtered with Ultrafree-0.5 units (Millipore, MW cut-off 10,000 Da) by centrifugation for 20 min at 12,000 g. The filtrate was acidified by dilution 1:1 with 0.1% trifluoroacetic acid (TFA) in water prior to solid-phase extraction (SPE). Cartridges tC 18 Sep-Pak Plus (Waters Corp., Milford, Mass.) were conditioned with 2 ml 0.1% TFA in acetonitrile followed by equilibration with 2 ml 0.1% TFA in water. One ml of the diluted filtrate was applied onto the SPE-cartridge and washed with 2 ml 0.1% TFA in water.

The elution of the peptides was achieved with 2 ml 70% acetonitrile, 0.1% TFA in water. The eluate was dried to completeness in a Speedvac concentrator and stored at −20° C. until further use. Sample pre-purification was needed to remove compounds, which interacted negatively with the analytes of interest.

Liquid Chromatography (LC) and Mass Spectrometry (MS) Analysis

The dried sample was re-dissolved in 0.1% TFA, sonicated for 15 min and centrifuged. An equivalent of 12.5 μl of the initial fermented milk was injected onto the HyperCarb column (0.32×150 mm, 5 μm) a 100% porous graphitic carbon column (HyperCarb column, Thermo Electron Corp., Bellefonte, Pa.). The column was installed on a HPLC system consisting of a Rheos 2000 pump (Flux Instruments, Switzerland) and a HTC PAL auto sampler (CTC Analytics, Switzerland).

The outlet of the column was directly coupled to a LCQ classic ion trap MS (Thermo Electron Corp., Bellefonte, Pa.). Solvent A consisted of 0.1% TFA in water and solvent B was 80% acetonitrile, 0.1% TFA in water. Peptide elution included an isocratic wash for 10 min with 100% solvent A followed by a linear gradient from 0-50% B in 30 min at a flow rate of 5 μl/min. The column was regenerated by a wash at 100% B for 5 min and then re-equilibrated for 15 min prior to the next injection.

The MS system was scanned from m/z 250-1600 at unit resolution; capillary voltage was set to 4 kV and temperature to 140° C. System control and data analysis was done with Xcalibur 1.3 using manual integration of the mass traces (extracted mass of m/z 312.1 for VPP and m/z 326.1 for IPP) from the MS chromatogram. The integrated areas of the standard peaks (in triplicate) were used as single calibration points to calculate the content of the two tripeptides in the samples.

If sample filtration with Ultrafree-0.5 units (10,000 Da cut-off) was omitted, peak shapes and intensities were drastically reduced and quantification of both peptides was not feasible (data not shown). Careful sample purification and adapted chromatographic conditions were critical to obtain reproducible and quantitative results. The specificity of MS detection is required to measure both peptides in the complex mixture of fermented products.

Results

The results show that most of the selected strains produced less than 1 mg/L of tripeptides (Table 1). Among the different lactic acid bacteria tested, only some strains of *L. helveticus* produced more than 1 mg/L up to almost 5 mg/L for LH111. There is no direct correlation between the proteolytic characteristics of the strains and the production of the tripeptides.

TABLE 1

Quantification of VPP + IPP produced by different strains of *S. thermophilus* (Sfi and S), *L. delbrueckii* subsp *bulgaricus* (Yl, Lfi and LD) and *L. helveticus* (LH).

| N° | NCC | old code | PA | pep | coag | VPP + IPP |
|---|---|---|---|---|---|---|
| 1 | 1988 | Sfi9 | 5 | nd | 6 to 8 | <1 |
| 2 | 1029 | S97 | 31 | nd | 3 to 4 | <1 |
| 3 | 408 | Yl5 | 46 | nd | 3 to 4 | <1 |
| 4 | 502 | Lfi1 | 58 | nd | 3 to 4 | <1 |
| 5 | 556 | Lfi5 | 56 | nd | 3 to 4 | <1 |
| 6 | 576 | Yl30 | 66 | nd | 3 to 4 | <1 |
| 7 | 725 | LD8 | 5 | nd | >8 | <1 |
| 8 | 1322 | LH111 | 93 | 1 | >8 | 5 mg/L |
| 9 | 1618 | LH152 | 92 | 2 | 3 to 4 | <1 |
| 10 | 1649 | LH158 | 102 | 3 | 3 to 4 | 2.7 mg/L |
| 11 | 126 | LH24 | 65 | 3 | 6 to 8 | <1 |
| 12 | 690 | LH25 | 93 | 1 | >8 | 2.5 mg/L |
| 13 | 557 | LH3 | 91 | 1 | 4 to 6 | <1 |
| 14 | 768 | LH31 | 85 | 2 | 6 to 8 | <1 |
| 15 | 837 | LH39 | 67 | 4 | 6 to 8 | <1 |
| 16 | 563 | LH4 | 85 | 1 | 6 to 8 | <1 |
| 17 | 878 | LH45 | 60 | 1 | 6 to 8 | <1 |
| 18 | 886 | LH47 | 74 | 2 | 6 to 8 | <1 |
| 19 | 935 | LH53 | 82 | 1 | 6 to 8 | 3.4 mg/L |
| 20 | 2618 | LH63 | 88 | 2 | 6 to 8 | 1.2 mg/L |
| 21 | 1017 | LH66 | 59 | 2 | 6 to 8 | 1.4 mg/L |
| 22 | 119 | LH71 | 36 | 3 | >8 | <1 |
| 23 | 1104 | LH79 | 94 | 2 | 4 to 6 | <1 |
| 24 | 1156 | LH88 | 84 | 3 | 4 to 6 | <1 |
| 25 | 1163 | LH89 | 82 | 1 | 4 to 6 | <1 |
| 26 | 1176 | LH91 | 94 | 2 | 3 to 4 | <1 |
| 27 | 1182 | LH92 | 59 | 4 | >8 | 2.4 mg/L |
| 28 | 1199 | LH94 | 91 | 1 | 6 to 8 | <1 |
| 29 | 4016 | | nd | nd | 4 to 5 | 1.4 mg/L |
| 30 | 1643 | LH157 | 77 | 3 | 4 to 5 | 1 mg/L |

(PA: acidification power (NCC Bionumerics);
pep: low to high peptidase activity, 1-4;
coag: coagulation time in hours;
VPP + IPP: concentration in the product in mg/L;
nd: not determined)

Beside LH158, the strains producing high amount of tripeptides (LH111, LH25, LH53 and LH92) needed around 8 h to coagulate milk. These strains were then tested in the same conditions, but by increasing fermentation time to 24 h and 40 h. The results show that prolongation of fermentation time had variable effects on tripeptides production between the different strains of *L. helveticus* (FIG. 1). For LH25 only a slight increase was observed between 8 h and 40 h, whereas LH53 generated a large amount of the tripeptides between 8 h and 24 h.

In general, a decrease in the amount of tripeptides released was observed between 24 h and 40 h.

Three strains of *L. helveticus* have been found to produce high amount of the hypotensive tripeptides. Therefore, these strains should be able to generate a dairy product containing almost twice the amount of tripeptides present in the Calpis product (Ameal S™).

The invention claimed is:

1. Strains of *Lactobacillus helveticus* deposited at the CNCM, France, on Jun. 11, 2008, in accordance with the provisions of the Budapest Treaty which are *Lactobacillus helveticus* CNCM I-3997.

2. A fermented milk product comprising a lactic acid bacteria strain of *Lactobacillus helveticus* CNCM I-3997 and a mixture of tripeptides IPP, VPP and LPP.

3. A fermented milk product according to claim 2, wherein the ratio of tripeptides IPP, VPP and LPP is from about 2:1:1 to 1:1:1.

4. A fermented milk product according to claim 2, wherein the total amount of tripeptides is about 10 to 50 mg/l.

5. A fermented milk product according to claim 2, which is used in a form selected from the group consisting of diluted, concentrated, purified, dried and combinations thereof.

6. A fermented milk product according to claim 2, comprising vitamin D.

7. The fermented milk product according to claim 2, wherein the mixture of tripeptides IPP, VPP and LPP consists of IPP, VPP and LPP.

8. A food or pharmaceutical product comprising a fermented milk product comprising a lactic acid bacteria strain of *Lactobacillus helveticus* CNCM I-3997 and a mixture of tripeptides IPP, VPP and LPP.

9. A food or pharmaceutical product according to claim 8, wherein the food product is selected from the group consisting of food ingredient, pet food, and food supplement.

10. A food or pharmaceutical product according to claim 8 comprising vitamin D.

11. The food or pharmaceutical product according to claim 8, wherein the mixture of tripeptides IPP, VPP and LPP consists of IPP, VPP and LPP.

12. A method for treating hypertension comprising the steps of administering a therapeutically-effective amount of a composition comprising a fermented milk product comprising a lactic acid bacteria strain of *Lactobacillus helveticus* CNCM I-3997 and a mixture of tripeptides IPP, VPP and LPP to a patient having hypertension.

13. The method according to claim 12, wherein the mixture of tripeptides IPP, VPP and LPP consists of IPP, VPP and LPP.

* * * * *